United States Patent
Nugent et al.

(10) Patent No.: US 10,264,988 B2
(45) Date of Patent: Apr. 23, 2019

(54) APPARATUS AND METHOD FOR RECORDING NEURAL SIGNALS IN THE PRESENCE OF ARTIFACTS

(71) Applicant: The Charles Stark Draper Laboratory, Inc., Cambridge, MA (US)

(72) Inventors: Brian Nugent, Acton, MA (US); Robert Bousquet, Waltham, MA (US); Jesse J. Wheeler, Boston, MA (US); Andrew Czarnecki, Cambridge, MA (US); John Lachapelle, Princeton, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 310 days.

(21) Appl. No.: 15/160,500

(22) Filed: May 20, 2016

(65) Prior Publication Data

US 2017/0238828 A1 Aug. 24, 2017

Related U.S. Application Data

(60) Provisional application No. 62/298,699, filed on Feb. 23, 2016.

(51) Int. Cl.
*A61B 5/04* (2006.01)
*A61N 1/36* (2006.01)
*A61B 5/00* (2006.01)

(52) U.S. Cl.
CPC ........ *A61B 5/04001* (2013.01); *A61B 5/7203* (2013.01); *A61B 5/7225* (2013.01); *A61N 1/36139* (2013.01); *A61B 5/725* (2013.01)

(58) Field of Classification Search
CPC ....... A61B 5/725; A61B 5/04001; A61B 5/04; A61B 5/7225; A61N 1/36139
See application file for complete search history.

(56) References Cited

U.S. PATENT DOCUMENTS

| | | | | |
|---|---|---|---|---|
| 4,015,212 A | * | 3/1977 | Miyata | H03F 3/3044 330/255 |
| 4,365,204 A | | 12/1982 | Haque | |

(Continued)

OTHER PUBLICATIONS

International Search Report and Written Opinion dated May 4, 2017 in PCT Application No. PCT/US2017/018697.
(Continued)

*Primary Examiner* — David J. McCrosky
(74) *Attorney, Agent, or Firm* — McDermott Will & Emery LLP

(57) ABSTRACT

Systems and methods are disclosed herein for recording electrical signals in the presence of artifacts. The system and methods can employ multiple techniques for attenuating large, unwanted artifacts while preserving lower amplitude desirable signals. Aspects that can improve the recording of electrical signals in the presence of larger artifacts include particular electrode placement and spacing, high dynamic range amplification with good linearity, and signal blanking. Combinations of more or fewer techniques can be employed to achieve the desired attenuation of signal artifacts while preserving the desired signal. The systems and methods are suitable for recording neural signals in the presence of electrical stimulation signals.

20 Claims, 11 Drawing Sheets

(56) References Cited

U.S. PATENT DOCUMENTS

| | | | |
|---|---|---|---|
| 4,438,354 | A | 3/1984 | Haque et al. |
| 4,555,668 | A | 11/1985 | Gregorian et al. |
| 5,161,529 | A | 11/1992 | Stotts et al. |
| 5,954,756 | A | 9/1999 | Hemming et al. |
| 8,200,332 | B2 | 6/2012 | Libbus et al. |
| 8,620,420 | B2 | 12/2013 | Aksenova et al. |
| 2003/0097050 | A1 | 5/2003 | Baru Fassio |
| 2006/0189901 | A1 | 8/2006 | Flaherty et al. |
| 2011/0304397 | A1 | 12/2011 | Stanley |
| 2012/0154049 | A1* | 6/2012 | Hong ............ H03F 1/223 330/260 |
| 2014/0135638 | A1 | 5/2014 | Lisogurski et al. |
| 2014/0180052 | A1 | 6/2014 | Lo et al. |
| 2014/0371564 | A1 | 12/2014 | Anikeeva et al. |

OTHER PUBLICATIONS

Brown, Edgar A., et al. Stimulus-Artifact Elimination in a Multi-Electrode System, IEEE Transactions on Biomedical Circuits and Systems, vol. 2, No. 1, pp. 10-21, Mar. 2008.

Eftekhar, Amir, et al. Towards a Next Generation Neural Interface: Optimizing Power, Bandwidth and Data Quality, IEEE Biomedical Circuits and Systems Conference (BioCAS), Nov. 2010.

Heffer, Leon F. et al. A novel stimulus artifact removal technique for high-rate electrical stimulation, Journal of Neuroscience Methods, vol. 170, Issue 2, pp. 277-284, May 30, 2008.

Lopez, Carolina Mora, et al. A Multichannel Integrated Circuit for Electrical Recording of Neural Activity, With Independent Channel Programmability, IEEE Transactions on Biomedical Circuits and Systems, vol. 6, No. 2, pp. 101-110, Apr. 2012.

Nam, Yoonkey, A retrofitted neural recording system with a novel stimulation IC to monitor early neural responses from a stimulating electrode, J Neurosci Methods, vol. 178, Issue 1, pp. 99-102, Mar. 30, 2009.

O'Keefe, Derek T., et al. Stimulus artifact removal using a software-based two-stage peak detection algorithm, Journal of Neuroscience Methods, vol. 109, pp. 137-145, Sep. 2001.

Olsson III, Roy H., et al. Band-Tunable and Multiplexed Integrated Circuits for Simultaneous Recording and Stimulation With Microelectrode Arrays, IEEE Transactions on Biomedical Engineering, vol. 52, No. 7, pp. 1303-1311, Jul. 2005.

Temel, Yasin, et al. Treating brain disorders with neuromodulation, Science, vol. 347, No. 6229, pp. 1418-1419, Mar. 27, 2015.

Yazicioglu, Refet Firat, et al. A 60 µW60 nV/√Hz Readout Front-End for Portable Biopotential Acquisition Systems, IEEE Journal of Solid-State Circuits, vol. 42, No. 5, pp. 1100-1110, May 2007.

* cited by examiner

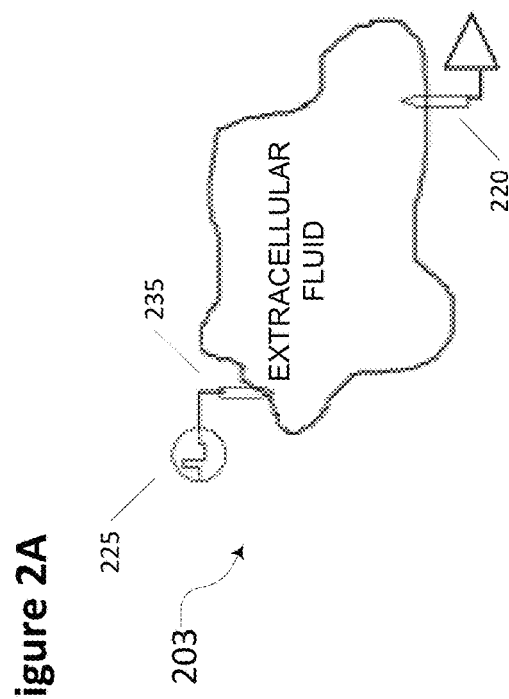
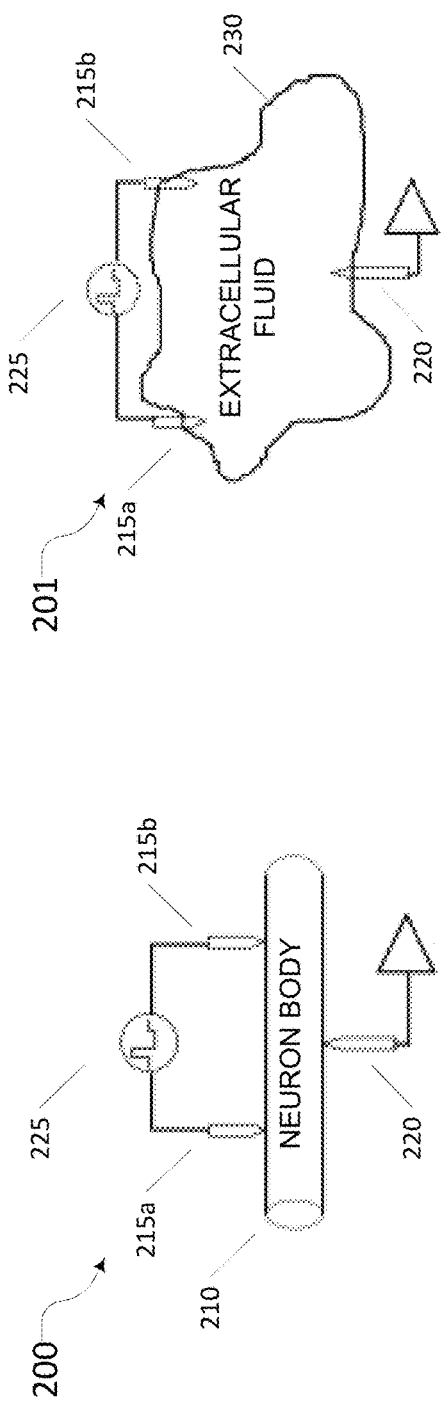
Figure 2A
Figure 2B
Figure 2C

APPARATUS AND METHOD FOR RECORDING NEURAL SIGNALS IN THE PRESENCE OF ARTIFACTS

CROSS-REFERENCE TO RELATED APPLICATIONS

The present application claims priority to U.S. Provisional Patent Application No. 62/298,699, entitled "APPARATUS AND METHOD FOR RECORDING NEURAL SIGNALS IN THE PRESENCE OF ARTIFACTS," filed Feb. 23, 2016, the entirety of which is hereby incorporated by reference.

GOVERNMENT LICENSE RIGHTS

This invention was made with government support under N66001-15-C-4019 awarded by the Defense Advanced Research Projects Agency (DARPA). The government has certain rights in the invention.

FIELD OF THE DISCLOSURE

The invention relates generally to detection of weak electrical signals in the presence of stronger signals, and more particularly to systems and methods for recording of neural signals in the presence of artifacts.

BACKGROUND OF THE DISCLOSURE

Peripheral and cortical neural stimulation are increasingly popular disease treatments. These techniques function by delivering a pulse to a targeted area in order to create a neural response. For example, peripheral neural stimulation can be used to treat chronic pain and migraines. Recent research has explored employing peripheral neural stimulation with an eye towards developing closed loop control of prostheses in order to enhance prosthetic limb systems for amputees. Cortical neural stimulation can be used to treat Parkinson's disease and depression.

Recording neural signals during stimulation is important for examining the neural response and adjusting stimulation parameters accordingly. Most neural recording amplifiers presented in literature focus on size and noise efficiency factor. These measures are driven by the desire to scale up the number of electrodes while keeping both power and chip size reasonable for implantation. Many examples have the amplifier connected directly to the electrodes by a bonding or flip chip process. Artifacts from the environment and stimulation pulse often contaminate the recording and overlap the neural signal. This makes it necessary for implanted neural amplifiers to handle unwanted artifacts from several sources including 60 Hz (and harmonics), movement noise in peripheral applications, and stimulation artifacts in neural stimulation applications.

Previous methods of recording a neural signal in the presence of such artifacts have suffered from several disadvantages. For example, optimization of amplifier gain for noise with no consideration of artifacts results in impressive bench results but poor in-vivo results. Similarly, post-processing of the neural signal assumes very high dynamic range amplifiers, typically discrete devices on PCBs, and therefore may not be effective with implanted neural amplifiers. Therefore, there is a need in the art for improved systems and methods for recording neural signals in the presence of artifacts.

SUMMARY OF THE INVENTION

The systems, methods and devices of this disclosure each have several innovative aspects, no single one of which is solely responsible for the desirable attributes disclosed herein.

One innovative aspect of the subject matter described in this disclosure can be implemented in a system for recording electrical signals in the presence of artifacts. The system can include a stimulation electrode configured to introduce a stimulation signal. The system can include a recording electrode configured to receive an electrical signal. The system can include a blanking circuit electrically coupled to the recording electrode, the blanking circuit comprising a switch in parallel with a capacitor, wherein the switch effectively shorts the capacitor when closed. The system can include an amplifier electrically coupled to the blanking circuit and configured to amplify the electrical signal, wherein the amplifier has a first gain when the switch is closed and a second gain lower than the first gain when the switch is open. The system can include a driver electrically coupled to the amplifier and configured to buffer the output of the amplifier.

In some implementations, the recording electrode is positioned at a distance from the stimulation electrode such that a stimulation signal emitted from the stimulation electrode is attenuated to a level at the recording electrode of between about one tenth and one thousandth of the initial signal magnitude.

In some implementations, the stimulation electrode comprises a first electrode and a second electrode. In such implementations, the first electrode and second electrode are configured to emit a stimulation signal at opposite polarities, and the recording electrode is positioned substantially equidistant from the first electrode and the second electrode.

In some implementations, the amplifier comprises: a first stage including a first differential amplifier; and a second stage including a second differential amplifier, a first push-pull circuit coupled to a first output of the second differential amplifier, and a second push-pull circuit coupled to a second output of the second differential amplifier.

In some implementations, the first stage comprises a first input FET, a second input FET, a first complementary FET coupled to the first input FET, and a second complementary FET coupled to the second input FET, wherein the first input FET and the second input FET are larger than the first complementary FET and the second complementary FET such that the first input FET and the second input FET have a lower thermal noise than the first complementary FET and the second complementary FET.

In some implementations, the first stage has a third gain set by a first capacitive feedback circuit and the second stage has a fourth gain lower than the third gain set by a second capacitive feedback circuit.

In some implementations, the second stage has higher thermal noise and/or lower power than the first stage.

In some implementations, the amplifier is a differential amplifier having a first output and a second output, and the driver comprises: a first complimentary input differential pair coupled to the first output; a second complimentary input differential pair coupled to the second output; a class A/B circuit coupled to the first complimentary input differential pair and the second complimentary input differential pair; and a push-pull circuit coupled to the class A/B circuit.

In some implementations, the driver has unity gain.

In some implementations, the system comprises a low-pass filter having a first cutoff frequency and a high-pass filter having a second cutoff frequency lower than the first cutoff frequency.

Another innovative aspect of the subject matter described in this disclosure can be implemented in a method of layered recording electrical signals in the presence of artifacts. The method can include emitting, by a stimulation electrode placed in proximity to a region of interest, a stimulation signal. The method can include receiving, by a recording electrode placed in proximity to the region of interest, an electrical signal responsive to the stimulation signal. The method can include amplifying, by an amplifier electrically coupled to the recording electrode, the electrical signal. The method can include reducing, by a blanking switch electrically coupled to the amplifier, a gain of the amplifier, the blanking circuit comprising a switch in parallel with a capacitor, wherein the switch effectively shorts the capacitor when closed, and wherein the amplifier has a first gain when the switch is closed and a second gain lower than the first gain when the switch is open. The method can include buffering, by a driver electrically coupled to the amplifier, the amplified signal. The method can include recording the buffered signal.

In some implementations, the method includes positioning the stimulation electrode at a distance from the stimulation electrode such that a stimulation signal emitted from the stimulation electrode is attenuated to a level at the recording electrode of between about one tenth and one thousandth of the initial signal magnitude.

In some implementations, the stimulation electrode includes a first electrode and a second electrode, the first electrode and second electrode configured to emit a stimulation signal at opposite polarities. In such implementations, the method further includes positioning the recording electrode substantially equidistant from the first electrode and the second electrode.

In some implementations, the method includes filtering the electrical signal by a filter electrically coupled to the amplifier, wherein the filter comprises a first cutoff frequency and a high-pass filter having a second cutoff frequency lower than the first cutoff frequency.

Details of one or more implementations of the subject matter described in this disclosure are set forth in the accompanying drawings and the description below. Other features, aspects, and advantages will become apparent from the description, the drawings and the claims. Note that the relative dimensions of the following figures may not be drawn to scale.

BRIEF DESCRIPTION OF THE DRAWINGS

The system and method may be better understood from the following illustrative description with reference to the following drawings in which:

FIGS. 2A-2C are block diagrams showing example electrode placements for recording neural signals.

DESCRIPTION OF CERTAIN ILLUSTRATIVE EMBODIMENTS

Figure 1:
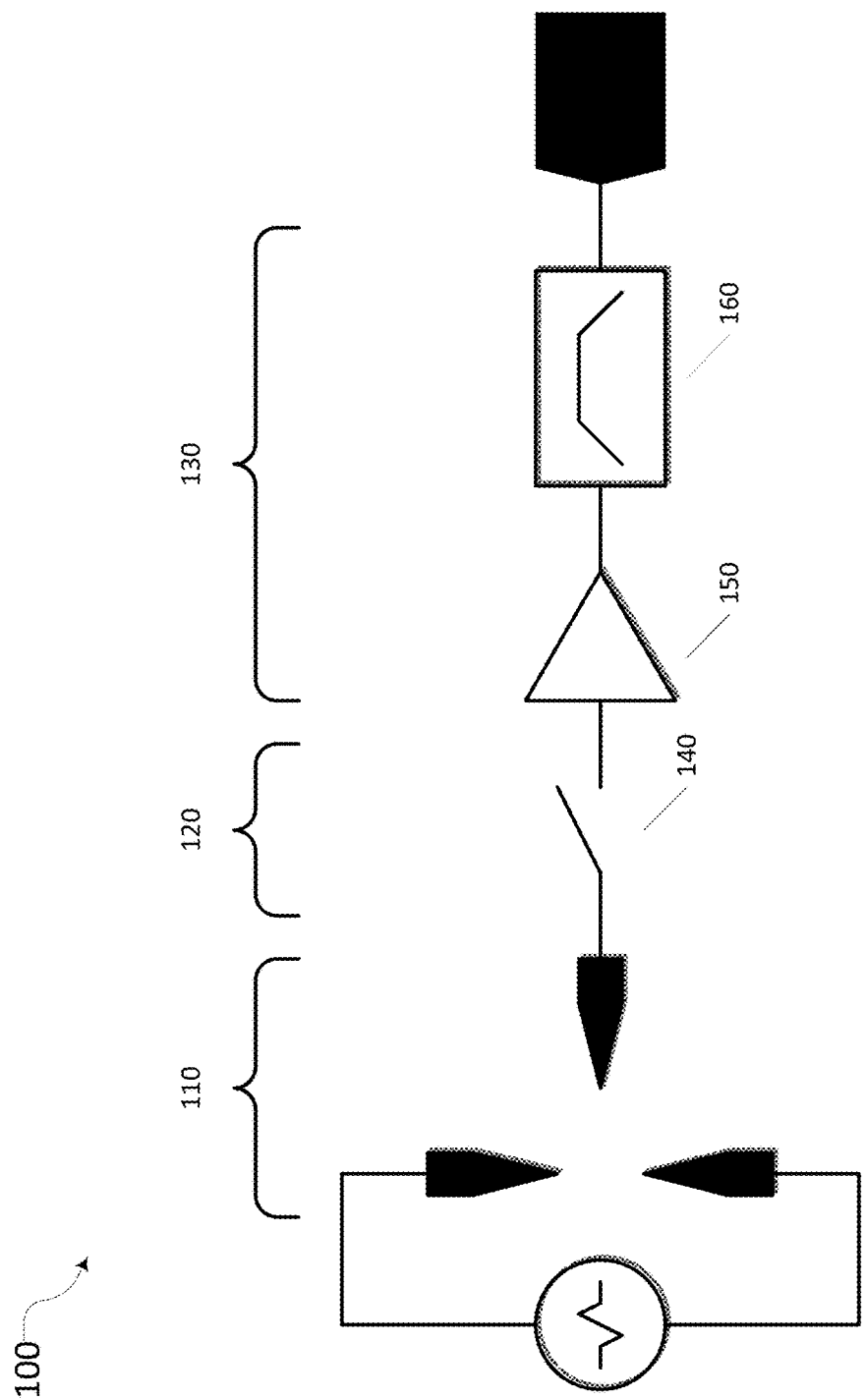
FIG. 1 is a block diagram showing an example system for implementing a method of recording neural signals in the presence of artifacts.

To provide an overall understanding of the invention, certain illustrative embodiments will now be described, including systems and methods for recording of neural signals in the presence of artifacts. However, it will be understood by one of ordinary skill in the art that the systems and methods described herein may be adapted and modified as is appropriate for the application being addressed and that the systems and methods described herein may be employed in other suitable applications, and that such other additions and modifications will not depart from the scope thereof.

A system for neural stimulation and recording can include stimulation signal circuitry, one or more stimulation electrodes, one or more recording electrodes, and recording circuitry. The stimulation signal circuitry can generate a stimulation signal. The stimulation electrodes can introduce the stimulation signal into tissue or cells. The stimulation signal can elicit a detectable response from the tissue or cells in the vicinity of the stimulation electrodes. The recording electrode may detect the responsive signal. The recording circuitry can process the detected signal. In one example application, the cells of interest may be neurons, which can emit a neural signal in response to the stimulation signal. The neural signal can be detected by the recording electrode. The detected neural signal may be low in amplitude. The recording circuitry may therefore include amplifier stages to amplify the detected neural signal.

In addition to detecting the neural signal, the recording electrode may detect a portion of the stimulation signal. The detected stimulation signal may lead to an artifact in the recorded signal. In some instances, the detected stimulation signal may have a much higher amplitude than the detected neural signal. If the amplitude of the detected stimulation signal is sufficiently large, it may saturate the amplifier stages of the recording circuitry. For example, a neural stimulation signal may have a current of 5 mA, which can produce up to 10 volts at the stimulation electrode. In contrast, the neural signal may have a much lower amplitude, on the order of several microvolts. Because the dynamic range for recording is typically tailored to the amplitude of the detected neural signal, the detected stimulation signal can saturate the amplifier stages and distort or obscure the detected neural signals.

No single approach can allow recording of a neural response signal down to 1 microvolt in the presence of a 10 volt stimulation signal. This disclosure therefore presents a layered approach that can provide protection of the neural signal via a combination of features. Such a layered approach can be thought of as a series of "moats," each moat allowing the neural response signal to pass while reducing the effect of the stimulation signal. The overall technique can combine several individual techniques that together can reduce the amplitude of stimulation signal artifacts enough to avoid amplifier saturation. A system employing several moats can reduce stimulation artifacts to a level relative to the neural response signal such that a reasonable analog-to-digital converter can process both signals simultaneously. The moats can include, without limitation, strategic electrode placement, blanking, and low amplifier gain combined with high amplifier dynamic range.

The disclosure presents several features that may be incorporated individually, or in various combinations, into systems and methods for neural signal recording including, without limitation:

(1) Consideration of neural signal processing in the presence of artifacts as a system problem to be solved in layers, wherein each layer contributes to a partial solution, and the combination of layers creates the total solution.
(2) Optimization of linear processing in the presence of artifacts, in contrast with previous approaches that optimized processing only for the neural signal in isolation.
(3) Enhanced high-speed blanking using the flexibility of an integrated circuit configuration of a neural amplifier, where the switches effectuating the blanking do not corrupt the recorded neural signal.
(4) Optimizing the frequency of the neural stimulation signal to balance therapeutic effectiveness with recording effectiveness.
(5) Filtering at different stages of the amplifier to reject frequencies not common in neural signals.

The techniques in this disclosure are presented for use in at least the following scenarios:

(1) Cortical closed loop recording where stimulation artifacts will be present during recording; for example, treatments for PTSD, Alzheimer's, and other maladies.
(2) Peripheral sensory neural recording in the presence of EMG signal artifacts which may be up to 60 dB higher than the sensory signals of interest.

FIG. 1 is a block diagram showing an example system 100 for implementing a method of recording neural signals in the presence of artifacts. The example system 100 shows an example set of "layers" for reducing the presence of artifacts in recorded neural signals. The example system 100 includes electrode placement 110, blanking 120, and amplifier settings and optional filtering 130. Electrode placement 110 is described in further detail below with regard to FIGS. 2A-2C. Blanking 120 via a blanking switch 140 is described in further detail below with regard to FIG. 3. Amplifier settings 130 for the amplifier 150 are described in further detail below with regard to FIGS. 4 to 7.

A system for recording of electrical signals in the presence of artifacts can include a stimulation electrode configured to introduce a stimulation signal, a recording electrode configured to receive an electrical signal, an amplifier to receive the electrical signal from the recording electrode and configured to amplify the electrical signal, a blanking switch at the input of the amplifier and configured to reduce a gain of the amplifier, a driver electrically coupled to the amplifier and configured to buffer the output of the amplifier, and an optional filter configured to filter the amplified electrical signal. The order of the elements of the system may vary. The system may only include a subset of these elements while still performing adequate processing of the neural signal in the presence of artifacts. The system may include additional elements that improve or enhance performance, usability, or ease of manufacture.

FIGS. 2A-2C are block diagrams showing example electrode placements 201-203 for recording neural signals. The electrode placements 201-203 can serve as the electrode placement 110 shown in FIG. 1. FIGS. 2A-2C can represent an example first layer, or first moat, of a method of recording neural signals in the presence of artifacts. These electrode placement approaches are considered one layer that can reduce the unwanted signal, insufficient by itself, but sufficiently for the additional layers to be used effectively. Electrode placement can be helpful, but may not be sufficient, to provide linearity in the signal processing path.

FIG. 2A is a block diagram showing one example electrode placement 200 for recording neural signals. FIG. 2A shows a single neural fiber 210 with stimulation electrodes 215a and 215b balanced to attenuate any unwanted signal detected by the recording electrode 220. In this configuration, the stimulation signal 225 can be applied in a bipolar fashion using the split stimulation electrodes 215a and 215b. The stimulation electrodes 215a and 215b can be positioned equidistant from the recording electrode 220, and can each emit the stimulation signal at an opposite polarity. Accordingly, the recording electrode 220 can be at, or close to, a low voltage node of the stimulation signal. Therefore, the stimulation signal apparent at the recording electrode 220 can be attenuated considerably.

All three of the stimulation electrodes 215a and 215b and the recording electrode 220 can be packaged in an integrated electrode assembly. For example, the stimulation electrodes 215a and 215b, and the recording electrode 220 can be aligned along an elongated rod- or strip-like structure with the recording electrode 220 located between the stimulation electrodes 215a and 215b. In other implementations, the electrodes can be arranged in a trident or triangle shape. The electrodes may be rigidly fixed to a structural component of the integrated electrode assembly, or extend from the assembly on flexible connections. The amplifier 150 and other electronics may reside in the integrated electrode assembly in proximity to the electrodes or in a separate electronics assembly coupled to the integrated electrode assembly by one or more wires or other interconnects. The system for recording of neural signals in the presence of artifacts can therefore include a stimulation electrode having a first electrode 215a and a second electrode 215b. The first electrode 215a and second electrode 215b can be configured to emit a stimulation signal 225 at opposite polarities. The recording electrode 220 can be positioned substantially equidistant from the first electrode 215a and the second electrode 215b. The stimulation electrodes 215a and 215b can be separated from each other by a distance of about between 0.01 mm and 10 mm. Depending on the geometry of electrode placement, the recording electrode 220 can be located between and equidistant the stimulation electrodes 215a and 215b, or separated from each stimulation electrode 215a and 215b by a distance of about between 0.01 mm and 10 mm.

FIG. 2B is a block diagram showing a second example electrode placement 201 for recording neural signals. FIG. 2B shows a more expansive electrode placement in extracellular fluid 230 around a basket of neurons. The approach of FIG. 2B is similar to FIG. 2A with respect to balancing the stimulation signal 225 so as to reduce the unwanted signal into the recording electrode 220. FIG. 2B shows an approach of physically separating the stimulation electrodes 215a and 215b and recording electrode 220 to attenuate the unwanted stimulation signal at the location of the recording electrode 220. The electrodes can be packaged in an integrated electrode assembly as was discussed in relation to FIG. 2A. The stimulation electrodes 215a and 215b can be separated from each other by a distance of about between 0.01 mm and 10 mm. Depending on the geometry of electrode placement, the recording electrode 220 can be located between and equidistant the stimulation electrodes 215a and 215b, or separated from the each stimulation electrode 215a and 215b by a distance of about between 0.01 mm and 10 mm.

FIG. 2C is a block diagram showing a third example electrode placement 203 for recording neural signals. FIG. 2C shows an example monopolar stimulation electrode configuration. The monopolar stimulation electrode configuration can include a single stimulation electrode 235 and a recording electrode 220. Attenuation of the stimulation signal can be accomplished by proper positioning of the recoding electrode 220 with respect to the stimulation electrode 235. That is, attenuation of the stimulation signal can be accomplished by distancing the recording electrode 220 from the stimulation electrode 235, while keeping it close enough to the region of interest to acquire neural signals responsive to the stimulation. The stimulation electrode 235 and the recording electrode 220 can be packaged in an integrated electrode assembly similar to that described with respect to FIG. 2A, but without a third electrode.

The signal voltage at the recording electrode 220 can be estimated from the stimulation current at the stimulation electrode 235, the tissue conductivity, and the distance between the recording electrode 220 and the stimulation electrode 235 using the formula $V=I_o/4\pi\sigma R$, where $\sigma$=tissue conductivity of ~3 mS/cm, $I_o$=injection current, and R=radius in meters. Thus, for a 5 mA pulse, in tissue, with the stimulation electrode 235 and recording electrode 220 separated by 1 mm, the voltage seen at the recording electrode 220 may be approximately 250 mV. Referring back to Moat 1 210 in FIG. 2, the attenuation due to an electrode separation of 1 mm can be from 10V to 250 mV. The system for recording neural signals in the presence of artifacts can therefore include a recording electrode 220 positioned at a distance from the stimulation electrode 235 such that a stimulation signal 225 emitted from the stimulation electrode 235 is attenuated to a level at the recording electrode 220 of between about one tenth and one thousandth of the initial signal magnitude. In another implementation, the recording electrode 220 can be positioned at a distance from the stimulation electrode 235 such that a stimulation signal 225 emitted from the stimulation electrode 235 is attenuated to a level at the recording electrode 220 of between about one tenth and one hundredth of the initial signal magnitude. In another implementation, the recording electrode 220 can be positioned at a distance from the stimulation electrode 235 such that a stimulation signal 225 emitted from the stimulation electrode 235 is attenuated by about 32 dB at the recording electrode 220. The recording electrode 220 can be separated from the each stimulation electrode 235 by a distance of about between 0.01 mm and 10 mm.

Figure 3:
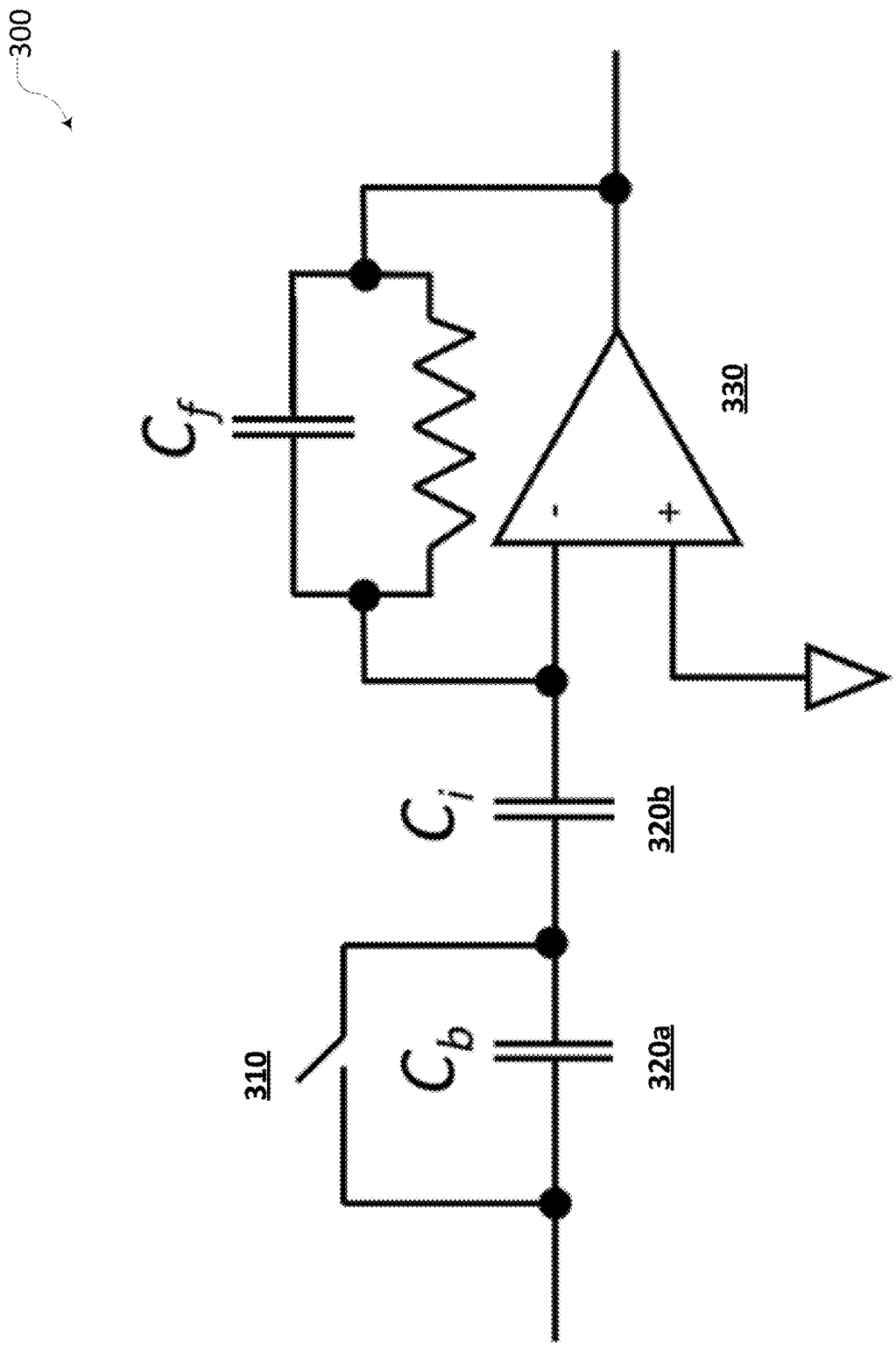
FIG. 3 is a block diagram showing an example blanking circuit for artifact attenuation.

FIG. 3 is a block diagram showing an example blanking circuit 300. Blanking can be used to reduce the effect of a strong stimulation artifact to prevent or limit saturating or clipping of the downstream electronics such as amplifiers and filters. Blanking can be used when there is prior knowledge of the signal; that is, blanking is appropriate when it can be synchronized to occur during a stimulation pulse. Traditional implementations of blanking performed blanking inside the feedback path of the amplifier. Such implementations attempted to reject artifacts by reducing the gain of the system at the time of stimulation, then returning to normal gain following stimulation. Although this method could avoid passing the stimulation signal through the analog processing chain, it perturbed a high impedance node in the feedback path. This resulted in long time constants for the system to recover.

The blanking circuit 300 avoids this issue by lowering the gain of an amplifier stage, but with a switch outside of the feedback path of the amplifier. In this manner, the amplifier stage and downstream electronics can be kept in the linear region to pass the neural signal undistorted. In an example implementation, a blanking switch 310 can used to introduce an input capacitor 320a between the recording electrode and an amplifier 330. Under normal operation, the blanking switch is closed and the signal gain is high. During a blanking period the switch 310 is opened and the input capacitor 320a is placed in series with the input capacitor 320b. The value of the input capacitor 320a $C_b$ is relatively small compared to the value of the input capacitor 320b $C_i$. Introduction of the input capacitor 320a increases the series impedance leading to the inverting node of the amplifier 330, which reduces the overall signal gain of the amplifier 330. This can allow high magnitude stimulation artifacts to propagate through the signal chain, but attenuated such that they do not saturate downstream amplifier stages. Blanking in this manner does not perturb the feedback loop of the amplifier 330, resulting in faster recovery times as compared to traditional methods. Thus, blanking in the manner of circuit 300 may only require a recovery time on the order of 1 ms. In contrast, the traditional method of performing blanking in the feedback path of the amplifier may require a recovery time on the order of 10 ms.

The blanking switch 310 can be added to any amplifier of the system. For any amplifier, it can perform the same function: limiting the gain of the amplifier to the linear region so that the amplifier does not have to recover from receiving a large signal. In some implementations, more than one amplifier of the system can employ a blanking switch. The blanking switch 310 can operate based on receipt of a control signal from an external controller. The blanking switch 310 can include any kind of solid-state switch or relay appropriate for the application. The blanking switch 310 can be incorporated into an ASIC along with the amplifier 140 and filter 160 shown in FIG. 1.

Figure 4:
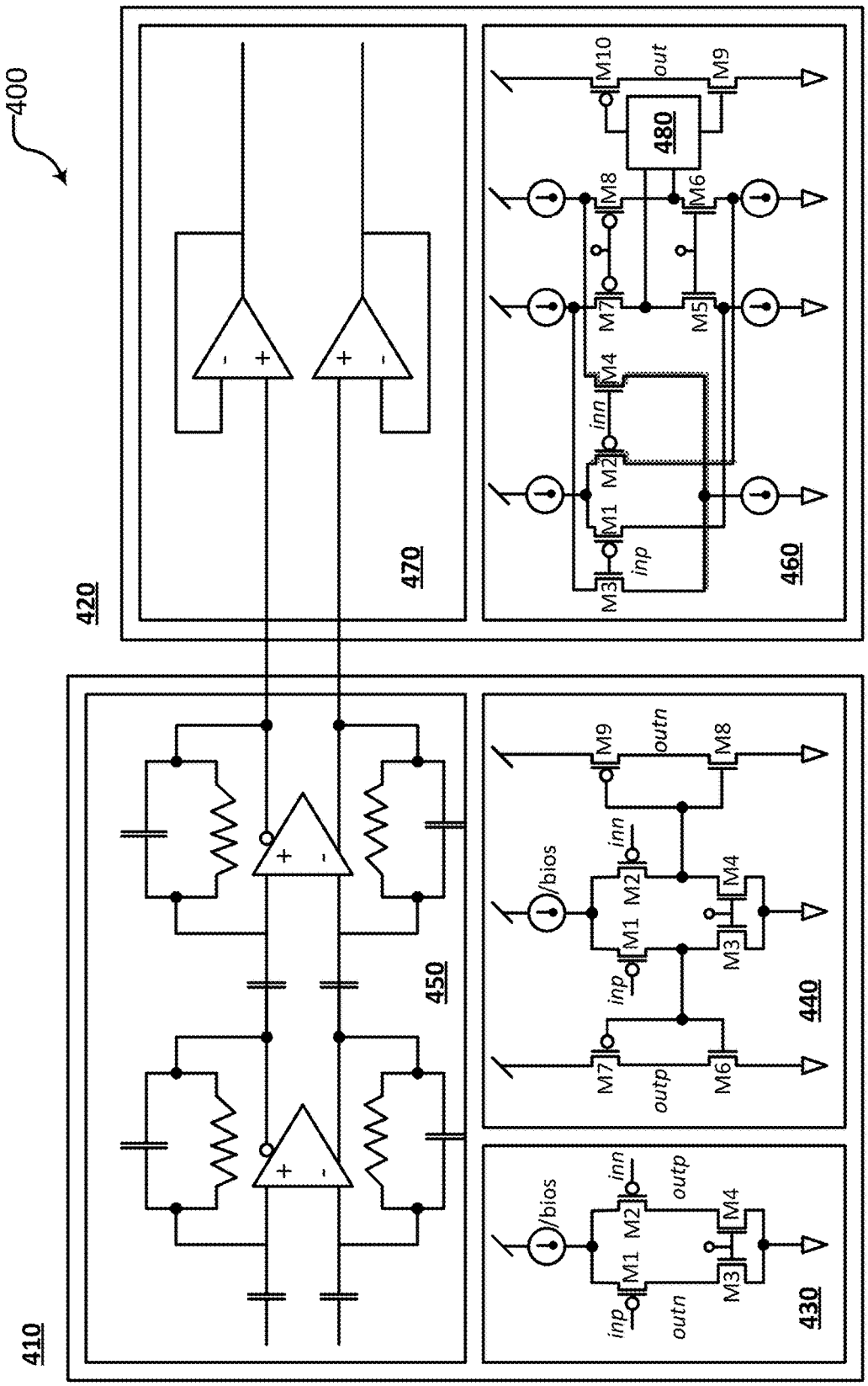
FIG. 4 is a block diagram showing an example amplifier circuit for processing neural signals.

FIG. 4 is a block diagram showing an example amplifier circuit 400 for processing neural signals. The amplifier circuit 400 can serve as the amplifier 150 shown in FIG. 1. The amplifier circuit 400 can be designed with gain, linearity, and dynamic range parameters to fulfill the requirements of the amplifier settings 130. The amplifier circuit 400 can include an amplifier 410 and an output driver 420. The amplifier 410 can be equipped with capacitive feedback circuits to increase the input impedance at the desired frequency—for example, 1 kHz—while maintaining the same gain ratio over all frequencies. The amplifier 410 can include a first-stage 430 and a second-stage 440. The amplifier block 450 can represent the combined first-stage 430 and second-stage 440. The driver block 470 can represent the buffer amplifiers of the output driver circuit 460.

In some implementations, the example amplifier circuit 400 can be designed with one or more, or all, of the following goals and constraints in mind:
1) Low Noise Front End: The first stage 430 should have the lowest noise and highest gain of the various stages, as its noise may contribute more to the ultimate noise of the system than the other stages. Having a low noise first stage 430 can increase the overall system's dynamic range. The first stage 430 can also have a modest output swing as compared to other stages.

2) High Output Voltage Swing Second Stage: The second 440 stage can use capacitive feedback to achieve higher input impedance. This provides less attenuation of gain from the first stage 430. It can have higher noise than the first stage 430 because its noise contributions relative to the input signal is reduced by the gain of the first stage 430. Power savings can be used towards having a higher output voltage swing as compared to the first stage 430. The gain of the second stage 440 can be lower than the first stage 430.

3) High Input Impedance Output Buffer: The buffer (or driver) stage 420 can have unity gain, high input impedance, and rail-to-rail inputs and outputs. It can include complementary input differential FET pairs and a push-pull output stage to provide increased dynamic range.

4) Capacitive Feedback: Capacitive feedback circuits can be used to increase input impedance while also preventing DC currents in the tissue surrounding the recoding electrodes. Such DC currents could harm the tissue.

Figures 7A, 7B:
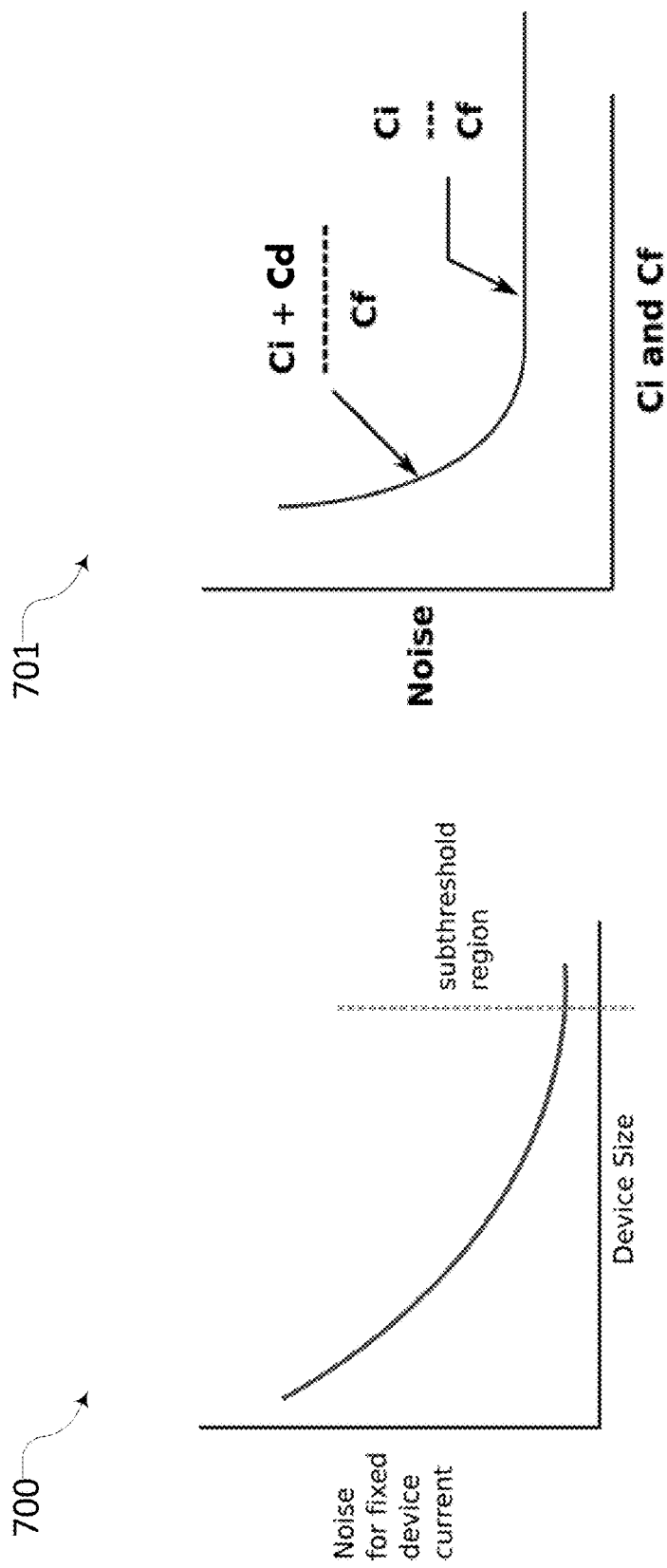
FIG. 7A shows an example graph of noise for fixed device current versus device size.
FIG. 7B is a graph showing an example plot of noise versus device size for devices in an example circuit for processing neural signals.

The first-stage 430 can form a low noise or low power gain stage. The first-stage 430 can include a differential amplifier having input FETs M1 and M2 and complementary FETs M3 and M4. The diagram of the first-stage 430 omits the feedback circuitry of the amplifier block 450 for the sake of simplicity. In the first-stage 430, the input field-effect transistor ("FET") M1 and M2 device size can be set to achieve the noise target at the desired frequency. FIG. 7B shows an example plot 701 of noise versus capacitance for devices in an example circuit for processing neural signals, where capacitance is a proxy for device size. The size of M1 and M2 in the first-stage 430 can be set such that the 1/frequency noise (pink noise) at the desired frequency—e.g., 1 kHz—contributed by M1 and M2 falls below a predetermined threshold. Devices M1 and M2 can operate in the subthreshold region which provides the highest ratio of transconductance per bias current. This can help reduce the thermal noise contributed by M1 and M2. The complementary FETs M3 and M4 should be sized such that the noise contribution of M3 and M4 is less than that of M1 and M2.

The second-stage 440 can include a wide-swing, push-pull output circuit. The second-stage 440 can include a differential amplifier having input FETs M1 and M2 and complementary FETs M3 and M4. The diagram of the second-stage 440 omits the feedback circuitry of the amplifier block 450 for the sake of simplicity. The second-stage 440 can include a first push-pull output circuit including FETs M6 and M7, and a second push-pull output circuit including FETs M8 and M9. Addition of the second-stage 440 to the first-stage 430 can yield several benefits. The push-pull configuration can enhance linearity of the overall amplifier 410. When implemented in conjunction with the first-stage 430, the second-stage 440 can achieve low total harmonic distortion, on the order of 1% at full scale output. The enhanced linearity combined with low distortion can allow the small but desirable neural signals to pass without distortion even in the presence of much larger stimulation artifact signals. The diagram of the second-stage 440 includes the devices of the first-stage 430, but omits the feedback circuitry of the amplifier block 450 for the sake of simplicity. The diagrams of both the first-stage 430 and the second-stage 440 omit the common mode feedback circuitry for simplicity.

The amplifier circuit 400 can also include an output driver 420. The output driver 420 can include a complementary input differential pair comprising FETs M1-M4 as shown in the output driver circuit 460. The complimentary input differential pair can couple to a class AB circuit 480. The output driver 420 can enable the high voltage output to drive sufficient current to downstream circuitry such as an analog-to-digital converter used to record the electrical signal.

The amplifier 410 can be fabricated using discrete transistors or in an integrated circuit. The amplifier 410 can be fabricated in pairs on a single die or an ASIC. Each amplifier 410 of the pair can receive an input signal from a recording electrode. The die or ASIC can include other elements of the system including output drivers, blanking switches, filters, etc.

Figure 5:
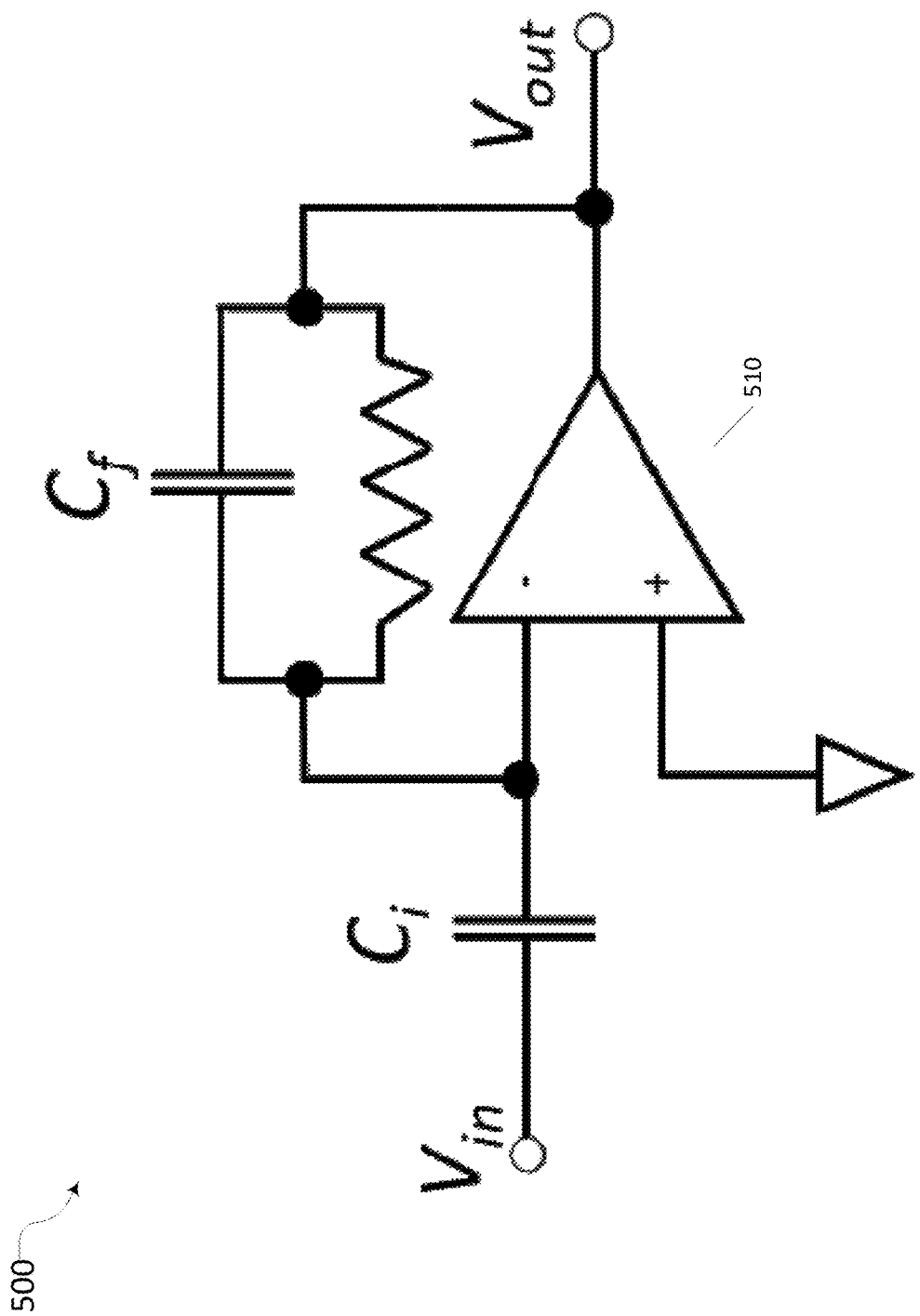
FIG. 5 is a block diagram showing an example circuit for processing neural signals.

FIG. 5 is a block diagram showing an example circuit 500 for processing neural signals. The example circuit 500 can serve as the amplifier block 450 shown in FIG. 4, but is shown single-ended for simplicity. The design considerations for the example circuit 500 are increased dynamic range and linearity. Increased dynamic range and linearity can allow the smaller neural signal to remain above the noise floor with ample headroom for the larger stimulation artifact to pass through the amplifier stages without saturating or clipping the amplifier, which could distort or obscure the smaller neural signal. The signal passing through the amplifier stages will thus contain both the desired neural signals and unwanted stimulation artifacts.

The example circuit includes an amplifier 510, a feedback capacitor $C_f$, and an input capacitor $C_i$. The input capacitor $C_i$ and feedback capacitor $C_f$ can be fabricated as metal-insulator-metal ("MIM") capacitors. The minimum feedback capacitance $C_f$ is constrained by technology. The minimum gain sets the input capacitance to: $g=C_i/C_f$; $C_i=g*C_f$. Thus, $C_i$ is constrained to $C_f$ times the minimum desired gain. The capacitance $C_i$ can be set to a level above this constraint to achieve the desired gain. In some implementations, the gain can be set to between 1 to 100. In some implementations the gain can be set to between 50 and 70. In some implementations, the first-stage gain can be between 10 and 25.

Figure 6:
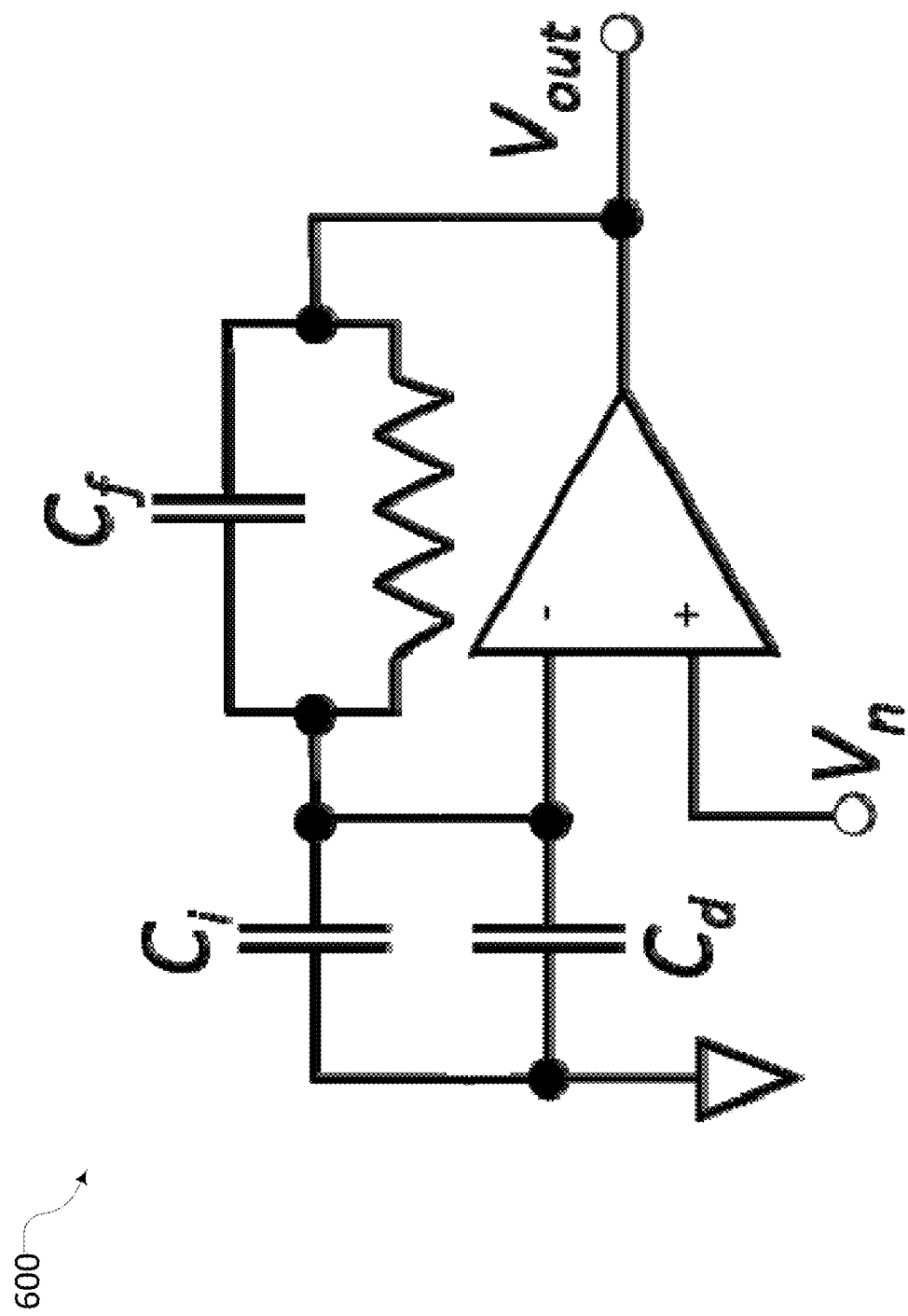
FIG. 6 is a block diagram showing an example circuit for processing neural signals.

FIG. 6 is a block diagram showing an example circuit 600 for processing neural signals. The example circuit 600, which includes the parasitic input capacitance $C_d$, can represent the amplifier 410 shown in FIG. 4. The example circuit 600 can show how the noise gain can be higher than the signal gain. In the example circuit 600, the gate capacitance of the input FET $C_d$ contributes to the noise gain by: $g_n=1+(C_i+C_d)/C_f$. The thermal noise level ($V_n$–10.7 nV/√Hz in this example application) sets the minimum device input transconductance, $g_m$. FIG. 7B shows an example plot 701 of noise versus capacitance for devices in the example circuit 600. The example plot 701 shows Noise versus $C_i$ and $C_f$, where the combined capacitance $C_i+C_f$ is a proxy for device size. In general, increasing the size of the input FETs will reduce their noise contribution, but increase parasitic capacitance $C_d$. To keep the noise gain from exceeding the signal gain significantly, $C_i$ must be increased until it is sufficiently larger than $C_d$. For sufficiently large value of $C_i$, $1+(C_i+C_d)/C_f \approx 1+C_i/C_f$. Thus, in addition to being constrained by $C_f$ and the minimum desired gain, $C_i$ is also constrained by $C_d$.

Figure 8:
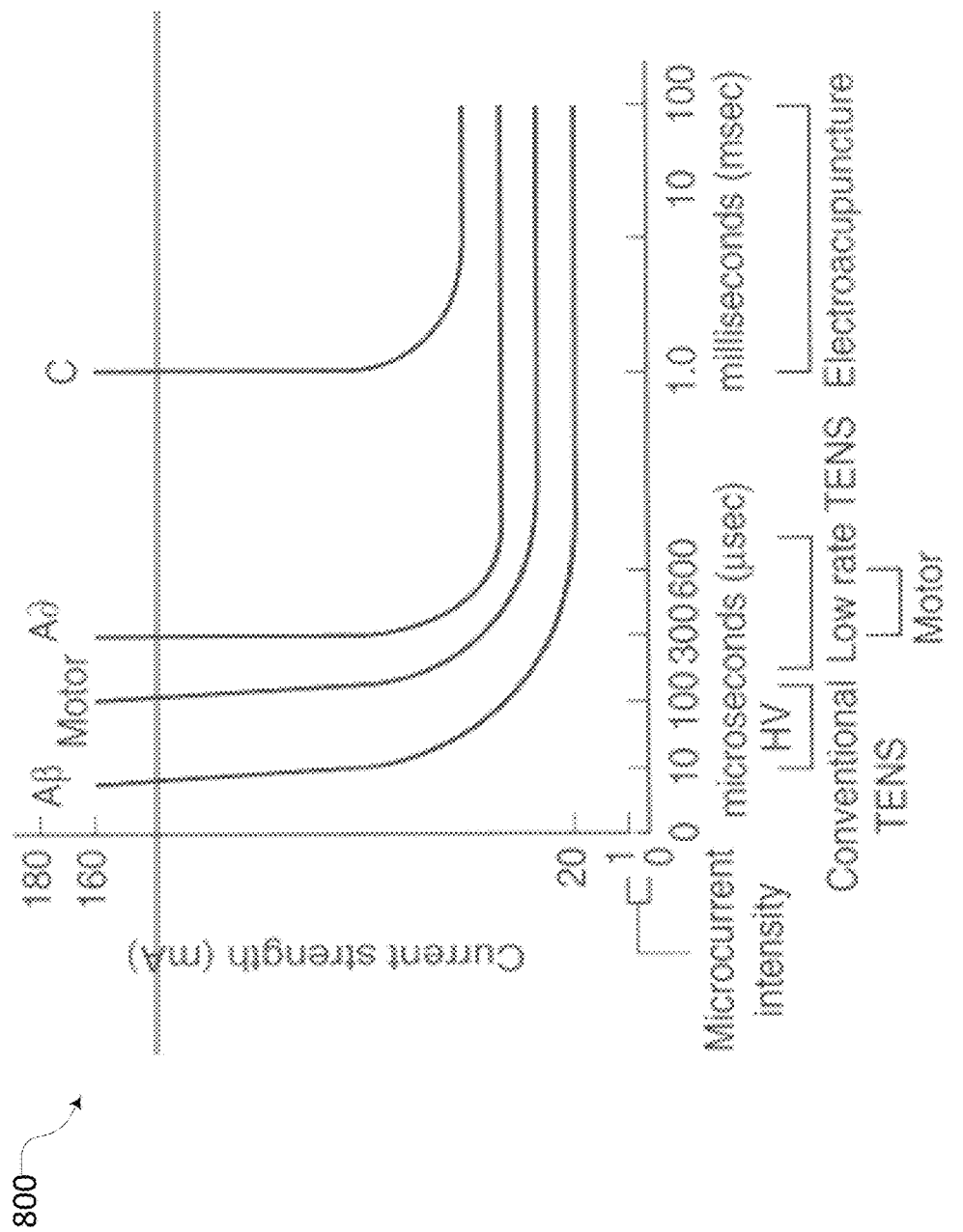
FIG. 8 is a graph showing example strength-duration curves of various stimulation signals.

FIG. 8 is a graph 800 showing example strength-duration curves of various stimulation signals. In addition to electrode placement as described above, artifacts can be reduced at the recording electrode 220 by careful design of the stimulation waveform. In previous approaches, the stimulation waveform structure was usually only modified to effect optimal treatment. In this constrained system, the stimulation waveform structure can be balanced both for positive effect on a patient, and effective neural recording. Current density, frequency, and duration can all be considered in addition to electrode placement. For example, setting the duration and intensity of the stimulation waveform at just above the threshold for effectiveness can excite the closest and largest fibers. Increasing intensity can excite smaller fibers and fibers farther away from the stimulation electrode. Similarly, increasing the stimulation waveform duration can also excite smaller fibers and fibers farther away; i.e., for the same intensity, increasing the stimulation waveform duration (e.g., by lower its frequency) can stimulate more fibers. Duration and intensity can thus be adjusted to optimize the extent of stimulation without causing larger than necessary artifacts in the recorded signal.

Figure 9B:
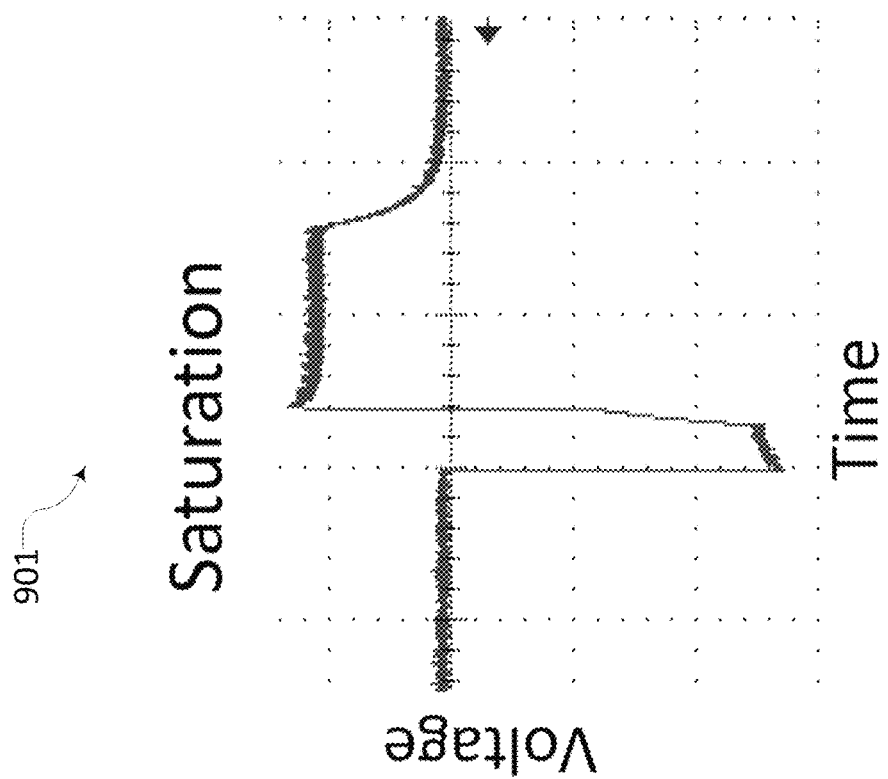
FIGS. 9A and 9B are graphs showing examples of amplifier output exhibiting saturation, and no saturation, respectively.
Figure 9A:
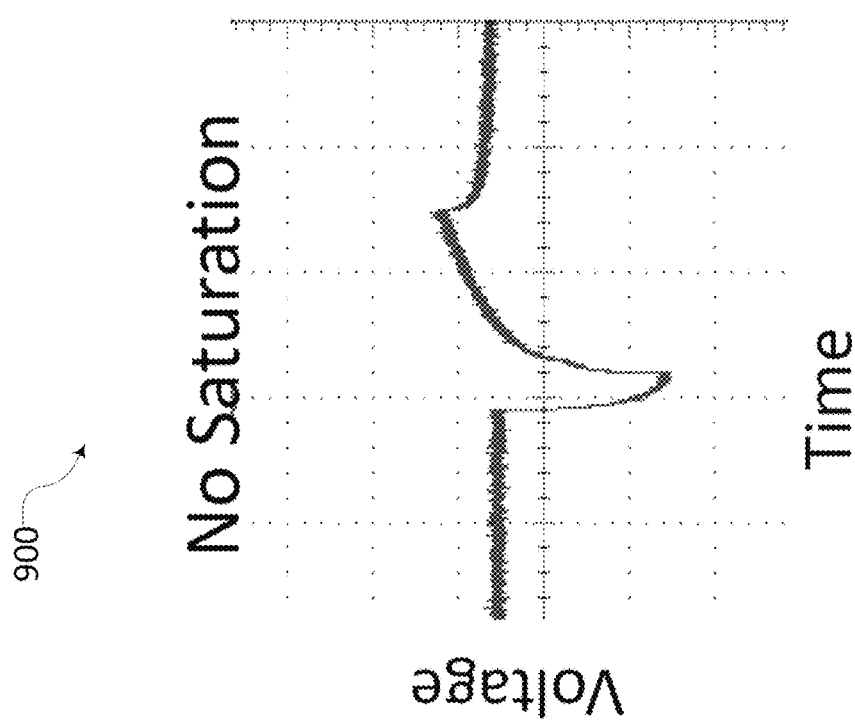

FIGS. 9A and 9B are graphs showing examples of amplifier output exhibiting no saturation (900), and exhibiting saturation (901). The graph 900 in FIG. 9A shows the output of an amplifier working within its dynamic range. The output is not distorted. The graph 901 in FIG. 9B shows the output of an amplifier exhibiting saturation. The saturation causes the signal to clip at both a high positive voltage and a high negative voltage. The dynamic range of neural recording amplifiers is typically small to accommodate the relatively low amplitude of neural response signals. Larger artifacts, such as those from a neural stimulation signal, can therefore cause saturation of the amplifier inputs. Once the amplifier is saturated, it requires a finite recovery time before it can pass a signal undistorted. The amplifier may not be able to effectively process the neural response signal during the recovery period. The neural response signal may thus be distorted or obscured.

Figure 10:
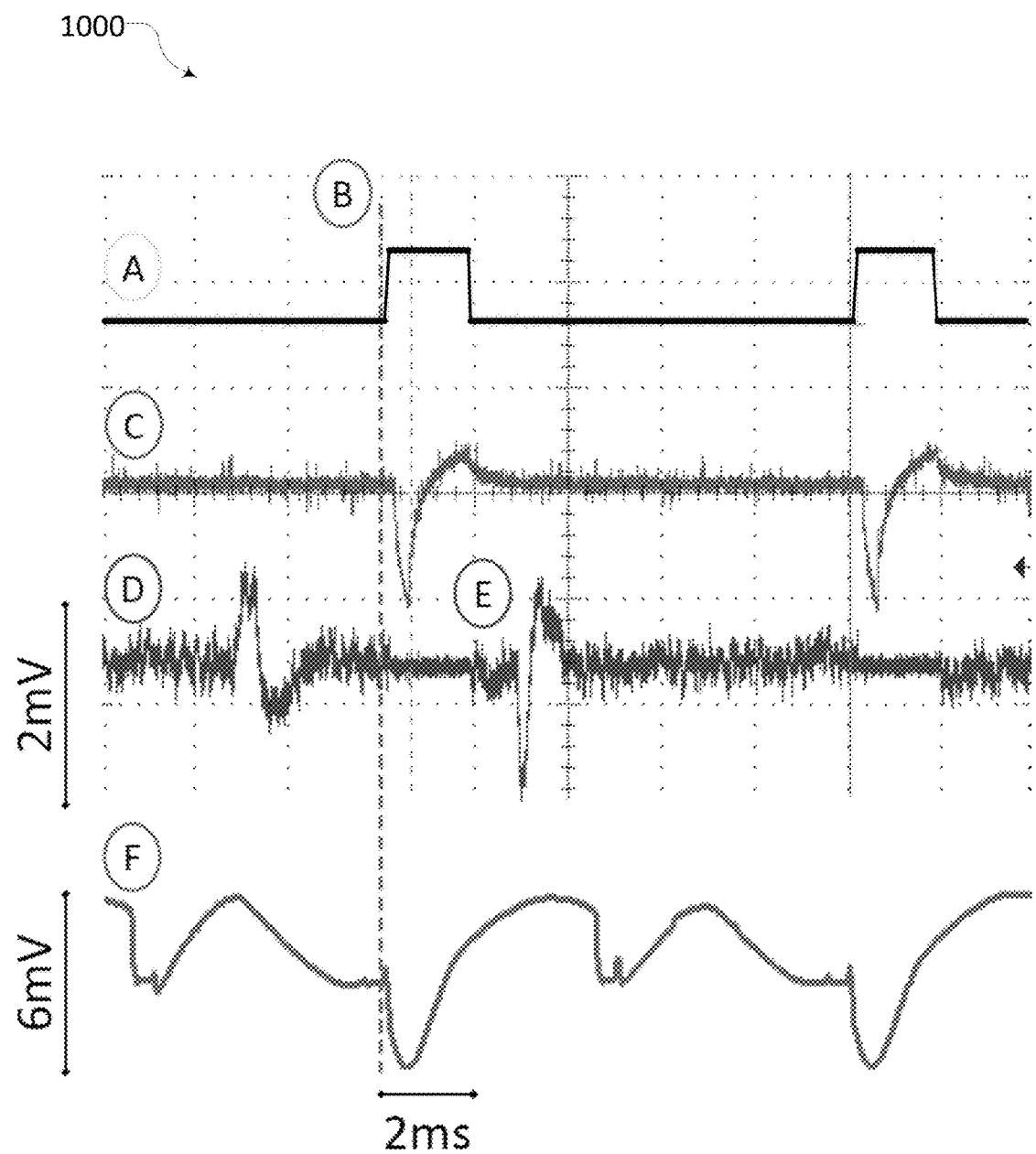
FIG. 10 shows a graph of example test results of recording neural signals in the presence of artifacts.

FIG. 10 shows a graph of example test results 1000 of recording neural signals in the presence of artifacts. The first signal (A) represents the blanking trigger. The second signal (C) represents the neural stimulation signal. The third signal (D) represents the output of a test amplifier designed and optimized as described in FIGS. 3-7. The fourth signal (F) represents the output of a commercially available amplifier with a bandwidth similar to the test amplifier.

The first signal (A) shows a point in time (B) just prior to the neural stimulation pulse. At (B), the first signal (A) transitions to high, initiating the blanking trigger. Shortly thereafter, the second signal (C) shows the neural stimulation pulse in the form of a negative voltage spike. During the period during which the blanking trigger (A) is high—about 2 ms in this example—the output of the test amplifier output remains flat, as shown in the third signal (D). After the blanking trigger ends at the end of the blanking period and the first signal (A) returns low, the test amplifier output (D) recovers in time to record the neural response signal (E). By comparison, the commercially available amplifier (F) experiences saturation during the stimulation pulse, and is still recovering during receipt of the neural response signal. The commercially available amplifier has too long of a recovery time to blank over each individual pulse, so it needs to blank over the duration of stimulation.

Figure 11:
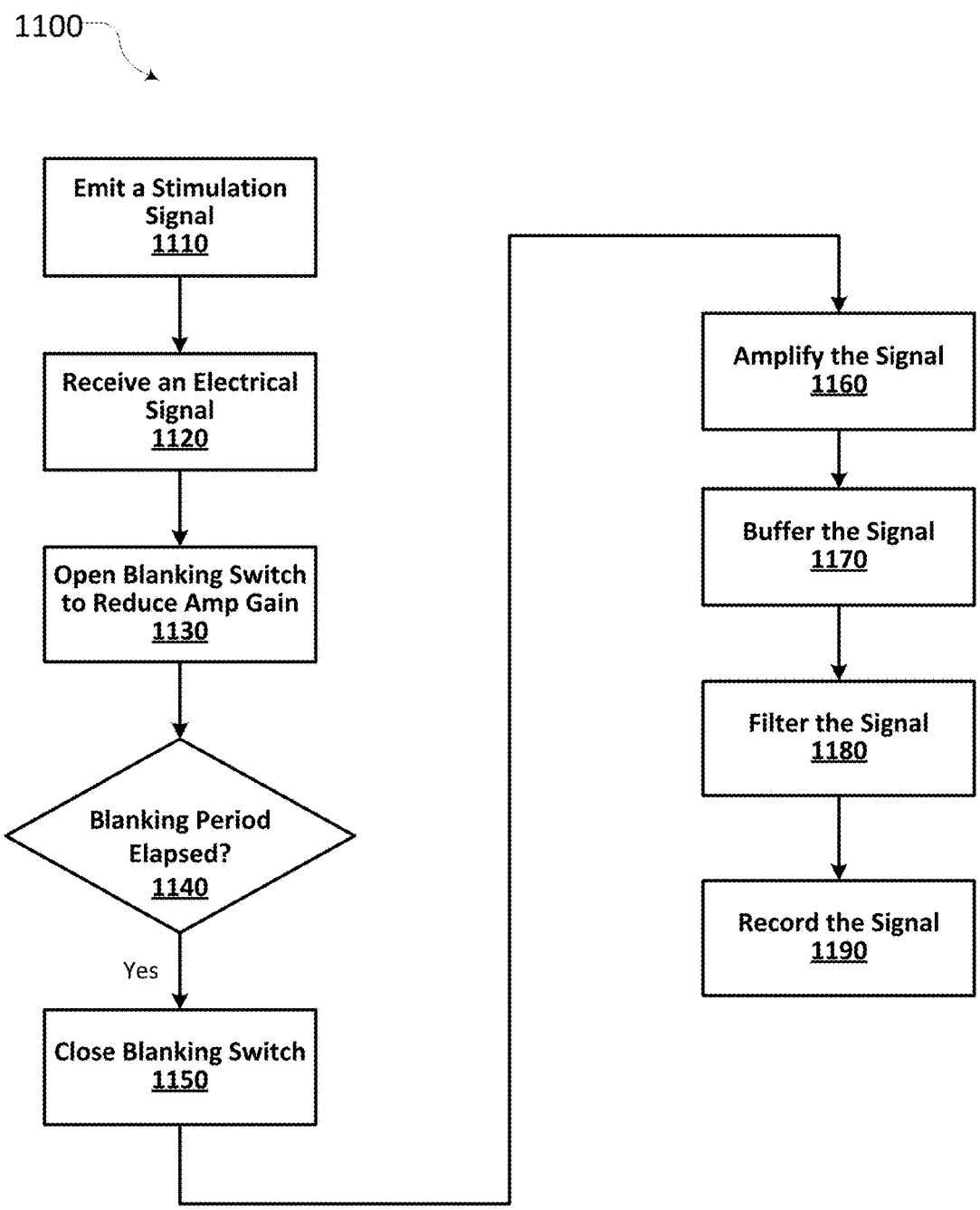
FIG. 11 is a flow chart showing an example method of recording neural signals in the presence of artifacts.

FIG. 11 is a flow chart showing an example method of recording neural signals in the presence of artifacts. The method can include emitting a stimulation signal (step 1110). The method can include receiving an electrical signal responsive to the stimulation signal (step 1120). The method can include opening the blanking switch to reduce a gain of the amplifier (step 1130). The method can include keeping the blanking switch open until a predetermined blanking period has elapsed (step 1140). The method can include closing the blanking switch when the blanking period has elapsed (step 1150). The method can include amplifying the electrical signal (step 1160). The method can include buffering the amplified signal (step 1170). The method can include filtering the electrical signal (step 1180). The method can include recording the buffered signal (step 1190).

The method can include emitting a stimulation signal (step 1110). The stimulation signal can be emitted by a stimulation electrode placed in proximity to a region of interest. As discussed above with regard to FIGS. 2A-2C and FIG. 8, the stimulation waveform structure can be balanced both for positive effect on patient, and effective neural recording. The stimulation waveform can then be emitted in a monopolar or bipolar fashion.

The method can include receiving an electrical signal responsive to the stimulation signal (step 1120). The electrical signal can be responsive to the stimulation signal. The electrical signal can be received by a recording electrode placed in proximity to the region of interest. The received electrical signal can include both the desired neural response signal as well as stimulation signal artifacts. The received electrical signal may include additional artifacts, such as electrical signals from motor neurons and skeletal muscles. The recording electrode can be positioned with respect to the stimulation electrode to balance adequate reception of the desired signal with optimal attenuation of the stimulation signal.

In some implementations, the method can further include positioning the stimulation electrode at a distance from the stimulation electrode such that a stimulation signal emitted from the stimulation electrode is attenuated to a level at the recording electrode of between about one tenth and about one thousandth of the initial signal magnitude. In some implementations, the attenuation can be set to any other desirable range.

In some implementations, the stimulation electrode can include a first electrode and a second electrode. The first electrode and second electrode can be configured to emit a stimulation signal at opposite polarities. In such implementations, the method can further include positioning the recording electrode substantially equidistant from the first electrode and the second electrode. Such positioning of the recording electrode with respect to the first electrode and the second electrode can achieve a significant attenuation of the stimulation signal.

The method can include opening a blanking switch to reduce a gain of the amplifier (step 1130). The blanking switch may be kept open until a predetermined blanking period has elapsed (step 1140). The method can include closing the blanking switch when the predetermined blanking period has elapsed (step 1150). Blanking was described in detail previously with respect to FIG. 3. Blanking in this manner can reduce an initial transient in the electrical signal caused by receipt of the stimulation signal at the recording electrode.

The method can include amplifying the electrical signal (step 1160). The electrical signal can be amplified by an amplifier electrically coupled to the recording electrode. The amplifier can include an amplifier as described above with respect to FIGS. 4 to 7. The amplifier can be designed for high dynamic range and linearity, and low noise. Such an amplifier can pass a small neural signal with low distortion even in the presence of much larger artifacts.

The method can include buffering the amplified signal (step 1170). The amplified signal can be buffered by a driver electrically coupled to the output of the amplifier. The driver can include a driver such as the output driver 420 described above with respect to FIG. 4. The driver, like the amplifier, can be designed for high dynamic range and linearity, and low noise. The driver can enable the high voltage output to drive sufficient current to downstream circuitry such as an analog-to-digital converter without loading the amplifier in a manner that could distort the neural signal or cause additional noise.

The method can include filtering the electrical signal (step 1180). Filtering can attenuate noise and artifacts at frequencies other than the frequency of the electrical signal of interest. Some noise and artifacts may be present at the frequency of the electrical signal of interest, so filtering may not be a complete solution to recording neural signals in the presences of artifacts, but filtering can help to attenuate a portion of the artifacts and/or noise.

Filtering can be accomplished with low-pass, high-pass, or band pass filters. Filtering can be performed at different points in the signal chain, including employing multiple filters at different points in the signal chain. For example, a low-pass filter and a high-pass filter can be placed at different points in the signal chain, possibly at distinct amplifiers. The goal of filtering is to avoid saturating amplifiers in the signal chain. Because an amplifier or filter later in the signal chain may be more likely to saturate, it may be beneficial to remove the louder unwanted frequencies earlier in the signal chain. For example, if artifacts are louder at frequencies below the frequency of interest, it may be beneficial to implement a high-pass filter earlier in the signal chain.

The filtering can be performed by one or more active filters implemented at one or more amplifiers. The filtering can be performed by one or more passive filters integrated with, preceding, or following one or more amplifier stages of the system. The filter can include any type of passive, active, analog, or digital filter appropriate for the application. The filter can be incorporated into an ASIC along with the amplifier and driver stages.

The method can include recording the filtered signal (step 1190). The recording can generally be performed by an analog-to-digital converter and a memory. If the method employs a digital filter, however, the signal has already been converted to digital, and recording the signal in this step may only require storing the digitized signal in memory. It is possible to record the signal onto an analog medium such as magnetic tape; however, processing of the neural signal in the presence of artifacts may require signal processing in the digital domain. The method is not limited to this exact sequence, and one or more of these steps may be duplicated, removed, or performed in a different sequence. For example, filtering and blanking may all occur with respect to a single amplifier, or may be performed in conjunction with different amplifiers, or separate from the amplifiers altogether.

While embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system for recording of electrical signals in the presence of artifacts, comprising:
   a stimulation electrode configured to introduce a stimulation signal;
   a recording electrode configured to receive an electrical signal;
   a blanking circuit electrically coupled to the recording electrode, the blanking circuit comprising a switch in parallel with a capacitor, wherein the switch effectively shorts the capacitor when closed;
   an amplifier electrically coupled to the blanking circuit and configured to amplify the electrical signal, wherein the amplifier has a first gain when the switch is closed and a second gain lower than the first gain when the switch is open; and
   a driver electrically coupled to the amplifier and configured to buffer the output of the amplifier, wherein:
   the blanking circuit is located between the recording electrode and an input to the amplifier.

2. The system of claim 1, wherein the recording electrode is positioned at a distance from the stimulation electrode such that a stimulation signal emitted from the stimulation electrode is attenuated to a level at the recording electrode of between about one tenth and one thousandth of the initial signal magnitude.

3. The system of claim 1, wherein the stimulation electrode comprises a first electrode and a second electrode, the first electrode and second electrode configured to emit a stimulation signal at opposite polarities, and the recording electrode is positioned substantially equidistant from the first electrode and the second electrode.

4. The system of claim 1, wherein the amplifier comprises:
   a first stage including a first differential amplifier; and
   a second stage including a second differential amplifier, a first push-pull circuit coupled to a first output of the second differential amplifier, and a second push-pull circuit coupled to a second output of the second differential amplifier.

5. The system of claim 4, wherein the first stage comprises a first input FET, a second input FET, a first complementary FET coupled to the first input FET, and a second complementary FET coupled to the second input FET, wherein the first input FET and the second input FET are larger than the first complementary FET and the second complementary FET such that the first input FET and the second input FET have a lower thermal noise than the first complementary FET and the second complementary FET.

6. The system of claim 4, wherein the first stage has a third gain set by a first capacitive feedback circuit and the second stage has a fourth gain lower than the third gain set by a second capacitive feedback circuit.

7. The system of claim 4, wherein the second stage has higher thermal noise and/or lower power than the first stage.

8. The system of claim 1, wherein the amplifier is a differential amplifier having a first output and a second output, and wherein the driver comprises:
   a first complimentary input differential pair coupled to the first output;
   a second complimentary input differential pair coupled to the second output;

a class A/B circuit coupled to the first complimentary input differential pair and the second complimentary input differential pair; and a push-pull circuit coupled to the class A/B circuit.

9. The system of claim 8, wherein the driver has unity gain.

10. The system of claim 1, further comprising a low-pass filter having a first cutoff frequency and a high-pass filter having a second cutoff frequency lower than the first cutoff frequency.

11. A method of recording of electrical signals in the presence of artifacts, comprising:

emitting, by a stimulation electrode placed in proximity to a region of interest, a stimulation signal;

receiving, by a recording electrode placed in proximity to the region of interest, an electrical signal responsive to the stimulation signal;

amplifying, by an amplifier electrically coupled to the recording electrode, the electrical signal;

reducing, by a blanking circuit electrically coupled to the amplifier, and located between an input to the amplifier and the recording electrode, a gain of the amplifier, the blanking circuit comprising a switch in parallel with a capacitor, wherein the switch effectively shorts the capacitor when closed, and wherein the amplifier has a first gain when the switch is closed and a second gain lower than the first gain when the switch is open;

buffering, by a driver electrically coupled to the amplifier, the amplified signal; and recording the buffered signal.

12. The method of claim 11, further comprising positioning the stimulation electrode at a distance from the stimulation electrode such that a stimulation signal emitted from the stimulation electrode is attenuated to a level at the recording electrode of between about one tenth and one thousandth of the initial signal magnitude.

13. The method of claim 11, wherein the stimulation electrode comprises a first electrode and a second electrode, the first electrode and second electrode configured to emit a stimulation signal at opposite polarities, the method further comprising:

positioning the recording electrode substantially equidistant from the first electrode and the second electrode.

14. The method of claim 11, wherein the amplifier comprises:

a first stage including a first differential amplifier; and a second stage including a second differential amplifier, a first push-pull circuit coupled to a first output of the second differential amplifier, and a second push-pull circuit coupled to a second output of the second differential amplifier.

15. The method of claim 14, wherein the first stage comprises a first input FET, a second input FET, a first complementary FET coupled to the first input FET, and a second complementary FET coupled to the second input FET, wherein the first input FET and the second input FET are larger than the first complementary FET and the second complementary FET such that the first input FET and the second input FET have a lower thermal noise than the first complementary FET and the second complementary FET.

16. The method of claim 14, wherein the first stage has a third gain set by a first capacitive feedback circuit and the second stage has a fourth gain lower than the third gain set by a second capacitive feedback circuit.

17. The method of claim 14, wherein the second stage has higher thermal noise and/or lower power than the first stage.

18. The method of claim 11, wherein the amplifier is a differential amplifier having a first output and a second output, and wherein the driver comprises:

a first complimentary input differential pair coupled to the first output;

a second complimentary input differential pair coupled to the second output;

a class A/B circuit coupled to the first complimentary input differential pair and the second complimentary input differential pair; and a push-pull circuit coupled to the class A/B circuit.

19. The method of claim 18, wherein the driver has unity gain.

20. The method of claim 11, further comprising filtering the electrical signal by a filter electrically coupled to the amplifier, wherein the filter comprises a low-pass filter having a first cutoff frequency and a high-pass filter having a second cutoff frequency lower than the first cutoff frequency.

* * * * *